United States Patent
Erman et al.

(10) Patent No.: US 7,189,760 B2
(45) Date of Patent: Mar. 13, 2007

(54) PHYSIOLOGICAL COOLING COMPOSITIONS CONTAINING HIGHLY PURIFIED ETHYL ESTER OF N-[[5-METHYL-2-(1-METHYLETHYL) CYCLOHEXYL] CARBONYL]GLYCINE

(75) Inventors: Mark B. Erman, Atlantic Beach, FL (US); Patrick J. Whelan, Fernandina Beach, FL (US)

(73) Assignee: Millennium Specialty Chemicals, Houston, TX (US)

( * ) Notice: Subject to any disclaimer, the term of this patent is extended or adjusted under 35 U.S.C. 154(b) by 474 days.

(21) Appl. No.: 10/817,770

(22) Filed: Apr. 2, 2004

(65) Prior Publication Data

US 2005/0222256 A1  Oct. 6, 2005

(51) Int. Cl.
*A61K 31/215* (2006.01)
*A61K 6/00* (2006.01)
*A61K 8/02* (2006.01)
*C07C 205/00* (2006.01)

(52) U.S. Cl. ............... 514/529; 560/125; 424/401
(58) Field of Classification Search .................. None
See application file for complete search history.

(56) References Cited

U.S. PATENT DOCUMENTS

| 4,060,091 A | 11/1977 | Watson et al. ............ 131/9 |
|---|---|---|
| 4,136,163 A | 1/1979 | Watson et al. ............ 424/54 |
| 4,150,052 A | 4/1979 | Watson et al. ............ 260/557 |
| 4,193,936 A | 3/1980 | Watson et al. ............ 260/557 |
| 4,226,988 A | 10/1980 | Watson et al. ............ 554/176 |

FOREIGN PATENT DOCUMENTS

| DE | 22 05 255 C3 | 11/1972 |
|---|---|---|
| DE | 25 03 555 A1 | 8/1975 |
| GB | 1 351 761 | 5/1974 |
| GB | 1 351 762 | 5/1974 |

OTHER PUBLICATIONS

Watson et al., "New Compounds with Menthol Cooling Effect," *J. Soc. Cosmet. Chem.*, vol. 29, No. 4, pp. 185-200 (1978).

*Primary Examiner*—Sikarl A. Witherspoon
(74) *Attorney, Agent, or Firm*—Jonathan L. Schuchardt; Needle & Rosenberg, P.C.

(57) ABSTRACT

The present invention provides, in one aspect, a substantially pure ethyl ester of N-[[5-methyl-2-(1-methylethyl)cyclohexyl]carbonyl]glycine. In another aspect, disclosed is a method for producing substantially pure ethyl ester of N-[[5-methyl-2-(1-methylethyl)cyclohexyl]carbonyl]glycine. In still another aspect, disclosed are various consumer products comprising the substantially pure ethyl ester of N-[[5-methyl-2-(1-methylethyl)cyclohexyl]carbonyl]glycine disclosed herein.

13 Claims, No Drawings

PHYSIOLOGICAL COOLING COMPOSITIONS CONTAINING HIGHLY PURIFIED ETHYL ESTER OF N-[[5-METHYL-2-(1-METHYLETHYL) CYCLOHEXYL] CARBONYL]GLYCINE

FIELD OF THE INVENTION

This invention relates generally to compositions comprising highly purified compounds possessing physiological cooling activity, methods for using, and methods for the production thereof.

BACKGROUND OF THE INVENTION

Physiological cooling agents (or coolants) are constantly gaining ground in various consumer applications due to their ability of improving desirable sensate properties of the products. The desired sensate properties are generally explained by the chemical action of such compounds on the nerve endings responsible for the sensation of cold. Common applications and uses for these compounds include, but are not limited to foods, beverages, flavors, pharmaceuticals, perfumes, and miscellaneous cosmetic goods.

One of the most well-known physiological coolants is l-menthol, a compound having the structure (1) shown below, and which has been used in several of the above mentioned applications for a very long time. In particular, l-menthol has an excellent cooling strength, low sensitivity threshold, and relatively low price.

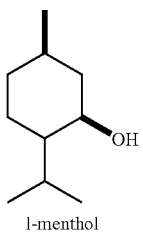

l-menthol

However, menthol also exhibits some undesirable properties, such as a strong "stinging" smell, a somewhat bitter taste, and it has relatively high volatility. These disadvantages of l-menthol have somewhat limited its utility in various applications and therefore stimulated an intense search for suitable physiological cooling agents that possess a low volatility and exhibit a relatively weak odor or even no odor at all.

The primary direction of physiological coolant compound research has focused toward the synthesis of molecules having a similar hydrocarbon skeleton as menthol, but which also comprise a much "heavier" functional group instead of the hydroxyl functional group. As a result, a number of synthetic menthol substitutes have been developed and commercialized. These substitutes include Menthyl Lactate (2), Menthyloxy Propane Diol (commonly referred to as "MPD") (3), Monomenthyl Succinate (4), and N-ethyl-p-menthane-3-carboxamide (commonly referred to as WS-3) (5).

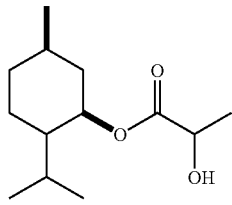

Menthyl Lactate

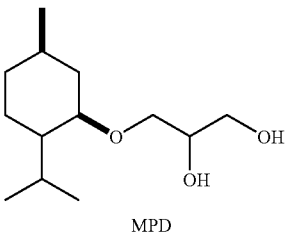

MPD

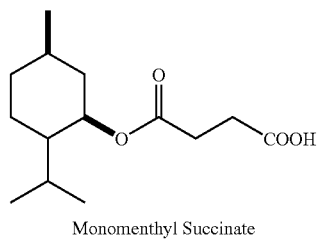

Monomenthyl Succinate

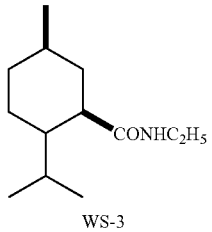

WS-3

WS-3 is widely considered to be the strongest of coolants 2 through 5 illustrated above and is representative of a larger group of N-monosubstituted p-menthane-3-carboxamides of the general structure 6 set forth below and which also potentially provide desirable coolant properties.

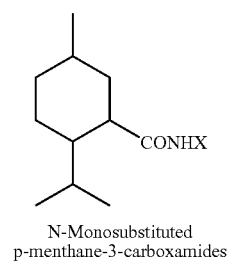

N-Monosubstituted
p-menthane-3-carboxamides

With specific reference to structure 6, substituent "X" is commonly selected from the lower linear or branched alkyl substituents, functionally substituted alkyl substituents, or aryl substituents. To that end, U.S. Pat. Nos. 4,060,091; 4,136,163; 4,150,052; 4,178,459; 4,193,936; and 4,226,988, the entire disclosures of which are hereby incorporated by reference for all purposes, give a comparison of cooling strengths of certain N-monosubstituted p-menthane-3-carboxamides numerically expressed as sensitivity thresholds in µg, wherein a lower threshold value correlates to a stronger coolant effect. Of the compared compounds, the only commercially used N-monosubstituted p-menthane-3-carboxamide compound is the WS-3 coolant, having a sensitivity threshold of 0.3 µg.

According to the above mentioned patent references, some N-monosubstituted p-menthane-3-carboxamides of general structure 6 above have proven to be stronger coolants than WS-3. For example compound 7, wherein X represents an m,p-dimethylphenyl substituent, has a sensitivity threshold of 0.1 µg; compound 8, wherein X represents an m-hydroxy-p-methylphenyl-substituent, has a sensitivity threshold of 0.1 µg; compound 9, wherein X represents a p-methoxyphenyl-substituent, has a sensitivity threshold of 0.1 µg, and a glycine derivative of structure 10, wherein X represents —CH$_2$COOC$_2$H$_5$, has a sensitivity threshold of 0.2 µg. Thus, compound 10 is 1.5 times stronger than WS-3 (compound 5).

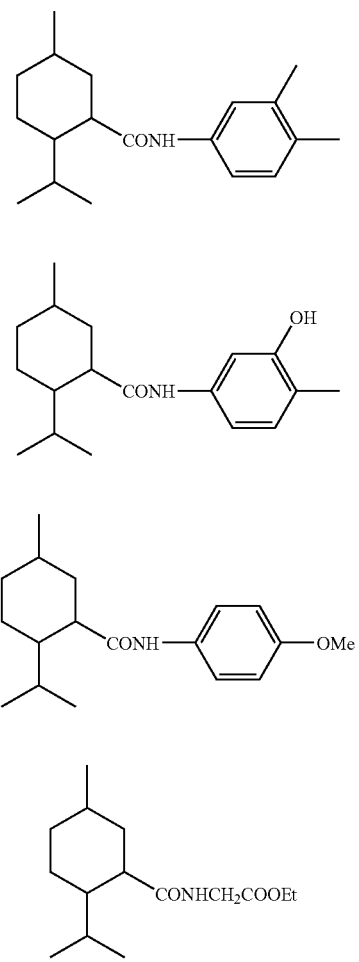

The absence of commercial interest in the compounds 7, 8 and 9 is recognized due to the toxicology considerations implicated by the presence of the benzene ring. However, it has been unclear why the glycine derivative 10 has not attracted commercial interest, especially in view of an article containing additional corrected data on the strength of p-menthane-3-carboxamide coolants, which reported that glycine derivative 10 actually had a sensitivity threshold of 0.13 µg, which is approximately 1.5 times stronger than compound 5, which actually had a 0.2 µg threshold (*J. Soc. Cosmet. Chem.*, 1978, vol. 29, pp. 185–200). To that end, the answer can be found in German reference DE 2,503,555, which teaches that compound 10 actually imparts a more bitter taste to a flavor composition when compared to a control.

Therefore, there is still a need in the art for a suitable physiological cooling agent possessing a high cooling activity.

SUMMARY OF THE INVENTION

The present invention is based upon the surprising discovery that the substantially pure ethyl ester of N-[[5-methyl-2-(1-methylethyl)cyclohexyl]carbonyl]glycine 10 is in the range of from approximately 2 to approximately 3 times stronger a physiological cooling agent than the commercially favored WS-3. Accordingly, in various aspects, the substantially pure ethyl ester of N-[[5-methyl-2-(1-methylethyl) cyclohexyl]carbonyl]glycine 10 is an at least 2.0, at least 2.5, or an at least 3.0 times stronger physiological cooling agent than the commercially favored WS-3.

Even more surprisingly, the substantially pure ethyl ester of N-[[5-methyl-2-(1-methylethyl)cyclohexyl]carbonyl]glycine does not exhibit a bitter taste or other adverse sensory effects previously thought. Therefore, it has been discovered that substantially pure ethyl ester of N-[[5-methyl-2-(1-methylethyl)cyclohexyl]carbonyl]glycine is suitable for use in a variety of consumer products wherein a physiological cooling effect is desired. Moreover, the compound 10 has a much lower volatility than menthol and is almost odorless, which adds to the advantages of using it in consumer goods.

In a first aspect, the present invention provides a composition comprising the ethyl ester of N-[[5-methyl-2-(1-methylethyl)cyclohexyl]carbonyl]glycine of the structural formula 10:

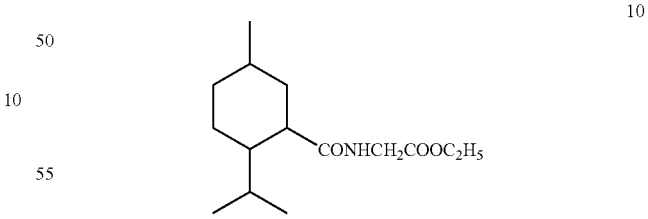

wherein, the ethyl ester of N-[[5-methyl-2-(1-methylethyl)cyclohexyl]carbonyl]glycine is present in substantially pure form.

In a second aspect, the present invention provides a composition comprising the ethyl ester of N-[[5-methyl-2-(1-methylethyl)cyclohexyl]carbonyl]glycine of the structural formula 10:

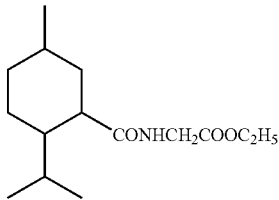

wherein the composition is substantially in the absence of impurities causing a bitter and/or sour after taste.

In still a third aspect, the present invention provides a method for the manufacture of the substantially pure ethyl ester of N-[[5-methyl-2-(1-methylethyl) cyclohexyl]carbonyl]glycine of structural formula 10

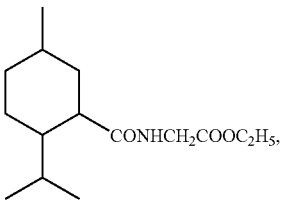

comprising the steps of providing the ethyl ester of N-[[5-methyl-2-(1-methylethyl) cyclohexyl]carbonyl]glycine in impure form; and purifying the impure ethyl ester of N-[[5-methyl-2-(1-methylethyl)cyclohexyl]carbonyl]glycine by at least one purification method comprising crystallization, sublimation, or precipitation, or a combination thereof, wherein the purification method is effective to provide the ethyl ester of N-[[5-methyl-2-(1-methylethyl)cyclohexyl] carbonyl]glycine in substantially pure form.

In still another aspect, the present invention provides the product produced by the method set forth above.

In still another aspect, the present invention provides a consumer product comprising the substantially pure ethyl ester of N-[[5-methyl-2-(1-methylethyl) cyclohexyl]carbonyl]glycine of the structural formula 10:

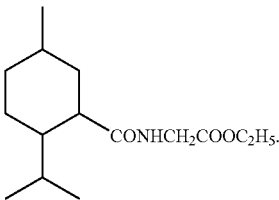

Additional advantages of the invention will be set forth in part in the description that follows, and in part will be obvious from the description, or may be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

DETAILED DESCRIPTION OF THE INVENTION

The present invention may be understood more readily by reference to the following detailed description, preferred embodiments of the invention and the Examples included therein. It is also to be understood that the various terminology used herein is for the purpose of describing particular embodiments only and is not intended to be limiting.

It must be noted that, as used in the specification and the appended claims, the singular forms "a," "an" and "the" include plural referents unless the context clearly dictates otherwise. Thus, for example, reference to "a solvent" includes mixtures of solvents.

Often, ranges are expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint.

In this specification and in the claims that follow, reference will be made to a number of terms that shall be defined to have the following meanings:

A weight percent of a component, unless specifically stated to the contrary, is based on the total weight of the formulation or composition in which the component is included.

"Optional" or "optionally" means that the subsequently described event or circumstance may or may not occur, and that the description includes instances where said event or circumstance occurs and instances where it does not.

As used herein, the term "impure" refers to N-[[5-methyl-2-(1-methylethyl) cyclohexyl]carbonyl]glycine ethyl ester comprising an impurity that imparts a bitter and/or sour after taste. Typically, an "impure" N-[[5-methyl-2-(1-methylethyl)cyclohexyl]carbonyl]glycine ethyl ester is less than or equal to 95.0% pure. Non-limiting examples of impurities known to impart a bitter and/or sour after taste include neomenthane-3-carboxylic acid, p-menthane-3-carboxylic acid, and mixtures thereof.

In accordance with the present invention, it has now been discovered that the undesired bitter taste associated with compound 10 can be attributed to impurities that result from the known processes for the manufacture of compound 10. More specifically, DE 2,205,255; GB 1,351,761; U.S. Pat. No. 4,150,052; U.S. Pat. No. 4,178,459; U.S. Pat. No. 4,193,936; and U.S. Pat. No. 4,226,988 (Watson et al.) teach a method of obtaining of compound 10 by a reaction of p-menthane-3-carboxylic chloroanhydride 11 with glycine ethyl ester hydrochloride 12 in the presence of NaHCO$_3$ in ether.

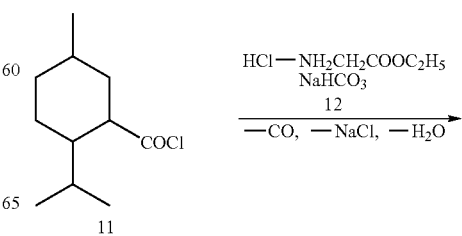

-continued

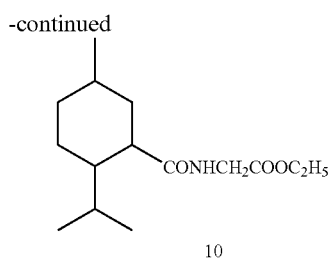

10

After the reaction, the ether layer was dried over MgSO$_4$ and distilled in vacuum, providing, according to DE 2,205,255, a product boiling at 150–162° C./0.1 torr, or according to U.S. Pat. No. 4,193,936 a product boiling at 150–152° C./0.1 torr as a liquid which rapidly solidified.

Significantly, in accordance with one aspect of the present invention, it has been discovered that these procedures fail to produce a compound having a purity higher than 93%. Specifically, the present invention has also discovered that the distilled final product contains traces of by-product neomenthane-3-carboxylic acid, p-menthane-3-carboxylic acid and a number of co-distilling unknown impurities, some or all of which impart a bitter and/or sour after taste and act to reduce the cooling strength of the coolant compound. Moreover, the present invention has further discovered that even after an additional redistillation step, the purity of the compound 10 still does not exceed 95%, which adversely affects the organoleptic properties of the product and has rendered the compound of structure 10 undesirable for commercial use.

Therefore, in one aspect, the present invention provides a composition comprising the ethyl ester of N-[[5-methyl-2-(1-methylethyl)cyclohexyl]carbonyl]glycine, having the general structure of formula 10:

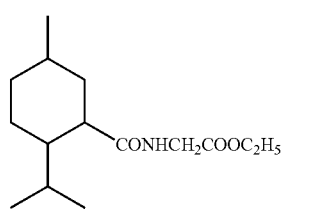

10 wherein the ethyl ester of N-[[5-methyl-2-(1-methylethyl)cyclohexyl]carbonyl]glycine is present in substantially pure form.

As used herein, the phrase "substantially pure" refers to the ethyl ester of N-[[5-methyl-2-(1-methylethyl)cyclohexyl]carbonyl]glycine in the substantial absence of impurities that impart a bitter and/or sour after taste. Typically, substantially pure is at least about 96.0% pure ethyl ester of N-[[5-methyl-2-(1-methylethyl)cyclohexyl]carbonyl]glycine. Under certain conditions, the purity level can be lower than 96.0%, such as where a high content of inert material that does not impact a bitter and/or sour after taste is present. In other aspects, the purities can be at least 97.0%, at least 98.0%, at least 99.0%, or at least 99.5%. The upper limit of purity can be as high as about 100%, depending upon the level of purification employed.

It should also be understood that "substantially pure," as defined herein, can in one aspect include a sum of any one or more stereoisomers of the ethyl ester of N-[[5-methyl-2-(1-methylethyl)cyclohexyl]carbonyl]glycine. Suitable isomers include isomer 10a having the 1-menthyl configuration, isomer 10b having a neomenthyl configuration, isomer 10c having an isomenthyl configuration, and isomer 10d having the neoisomenthyl configuration.

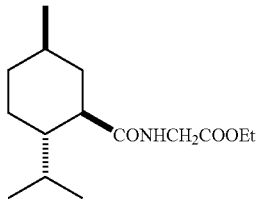

10a

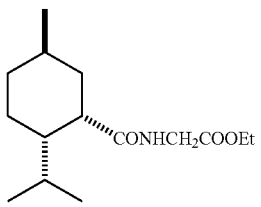

10b

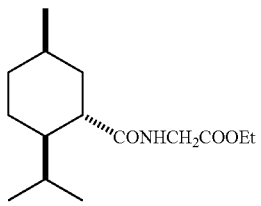

10c

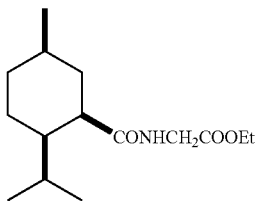

10d

Also included within the defined scope of substantially pure are any one or more of isomers 13a–d which represent the four enantiomers of structures 10a–d above.

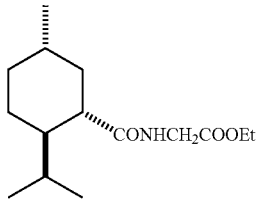

13a

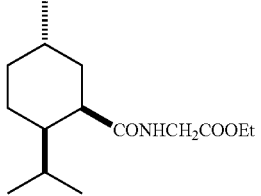

13b

-continued

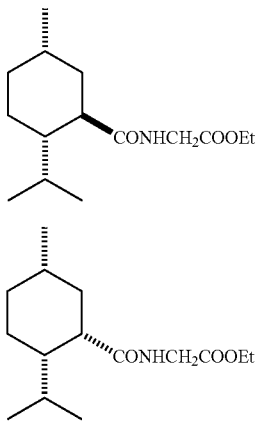

Accordingly, in various aspect, the ethyl ester of N-[[5-methyl-2-(1-methylethyl) cyclohexyl]carbonyl]glycine of the formula 10 is at least purified to a level of at least 96%, at least 97%, at least 98%, at least 99%, or at least 99.5% concentration of the sum of stereoisomers 11a–d and 13a–d. In still another aspect, the ethyl ester of N-[[5-methyl-2-(1-methylethyl)cyclohexyl]carbonyl]glycine of the formula 10 is purified to a level of at least 96% concentration of only the 1-menthyl isomer 10a. In still other aspects, the substantially pure ethyl ester of N-[[5-methyl-2-(1-methylethyl)cyclohexyl]carbonyl]glycine of the formula 10 is at least 97%, at least 98%, at least 98.5%, at least 99%, at least 99.5%, or about 100% pure stereoisomer 10a.

In another aspect, the present invention provides a composition comprising the ethyl ester of N-[[5-methyl-2-(1-methylethyl)cyclohexyl]carbonyl]glycine, having the general structure of formula 10:

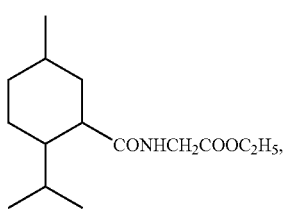

wherein the composition is substantially in the absence of impurities causing a bitter and/or sour after taste. By "impurities" it is intended that substantially all of the types of impurities, either from a single type of impurity or multiple impurities, as appropriate for the composition, that cause bitter and/or sour after taste, be substantially absent, thus leading to a composition that has a greatly reduced, nominal, or no bitter and/or sour after taste, compared to the impure composition. It is intended that "bitter and/or sour" refers to the purified composition being greatly reduced in or having only a nominal or, in fact, no bitter or sour taste as compared to the impure composition. In one aspect, the composition is substantially in the absence of neomenthane-3-carboxylic acid. In another aspect, the composition is substantially in the absence of p-menthane-3-carboxylic acid. In still another aspect, the composition is substantially in the absence of a mixture of neomenthane-3-carboxylic acid and p-menthane-3-carboxylic acid.

In still another aspect, provided is a method for the manufacture of the substantially pure ethyl ester of N-[[5-methyl-2-(1-methylethyl)cyclohexyl]carbonyl]glycine of structural formula 10

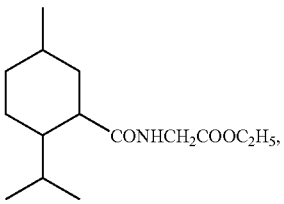

comprising the steps of: a) providing the ethyl ester of N-[[5-methyl-2-(1-methylethyl) cyclohexyl]carbonyl]glycine in impure form; and b) purifying the impure ethyl ester of N-[[5-methyl-2-(1-methylethyl)cyclohexyl]carbonyl]glycine provided in step a) by at least one purification method comprising crystallization, sublimation, or precipitation, or a combination thereof, wherein the purification method is effective to provide the ethyl ester of N-[[5-methyl-2-(1-methylethyl)cyclohexyl]carbonyl]glycine in substantially pure form.

Various methods for preparing the impure ethyl ester of N-[[5-methyl-2-(1-methylethyl)cyclohexyl]carbonyl]glycine are known in the art, and therefore, the reaction mechanism for providing an impure ethyl ester of N-[[5-methyl-2-(1-methylethyl) cyclohexyl]carbonyl]glycine will not be discussed in detail herein. However, it should be appreciated that suitable methods include, without limitation, the reaction of p-menthane-3-carboxylic chloroanhydride with glycine ethyl ester hydrochloride in the presence of NaHCO$_3$ in ether, such as disclosed in DE 2,205,255; GB 1,351,761; U.S. Pat. No. 4,150,052; U.S. Pat. No. 4,178,459; U.S. Pat. No. 4,193,936; and U.S. Pat. No. 4,226,988, the entire disclosures of which are hereby incorporated by reference for all purposes, and especially for the production of the impure compound 10.

Purification of the impure ethyl ester of N-[[5-methyl-2-(1-methylethyl) cyclohexyl]carbonyl]glycine compounds can be performed using general purification methods known in the art for purifying an organic compound, which include, but are not limited to, crystallization, recrystallization, precipitation, redistillation, sublimation, or a combination thereof. In one aspect, the purification step comprises crystallization or recrystallization of the ethyl ester of N-[[5-methyl-2-(1-methylethyl)cyclohexyl]carbonyl]glycine from an appropriate solvent.

Suitable solvents include, but are not limited to, an aliphatic hydrocarbon (for example heptane), an aromatic hydrocarbon (for example benzene, toluene, or a xylene), alcohol (for example ethanol), ester (for example ethyl acetate), ether (for example ethyl ether), ketone (for example acetone), chlorinated hydrocarbon (for example dichloromethane), or amide (for example dimethylformamide), or a mixture thereof.

In another aspect, the purification step comprises precipitation. According to this aspect, the precipitation step is performed by completely dissolving the impure compound in an appropriate solvent, for example methanol, followed by addition of an excess of a second solvent in which compound 10 has a poor solubility, for example water. Another example is ethanol or isopropanol as first solvent and heptane as the second solvent.

In still another aspect, the present invention provides consumer products comprising the substantially pure ethyl ester of N-[[5-methyl-2-(1-methylethyl) cyclohexyl]carbonyl]glycine of structure 10, as described herein. The purified compositions of the present invention can be used in any consumer good capable of using a cooling agent. In one aspect, the consumer goods comprising substantially pure ethyl ester of N-[[5-methyl-2-(1-methylethyl)cyclohexyl]carbonyl]glycine of structure 10 are suitable for human consumption. In another aspect, the consumer goods are suitable for topical application to mammalian skin, including without limitation, human as well as veterinary applications. More specific examples of consumer goods include, without limitation, flavor blends, foods, cosmetic preparations, confectionery, soft and alcoholic beverages, chewing gums, toothpaste, dental floss, mouthwash, anti-plaque, anti-gingivitis compositions, shampoos, antidandruff shampoos, lotions, deodorants, after shave lotions, shaving gels, shaving aid composites, fragrances, skin sanitizing compositions, throat lozenges, throat drops, chewable antacid tablets, or pharmaceutical compositions or medications, including anti-inflammatory compositions, compositions for treatment of nasal symptoms, for upper gastrointestinal tract distress, for treating cold symptoms, for cough relief, for alleviating discomfort of hot flash, or for throat therapy, and the like.

Compositions comprising the substantially pure compound of formula 10 can also be used in combination with accessory compounds that facilitate the incorporation of the substantially pure ethyl ester of N-[[5-methyl-2-(1-methylethyl)cyclohexyl]carbonyl]glycine into the above mentioned consumer goods. Examples of such accessory compounds include, but are not limited to, solvents such as ethanol or propylene glycol, control release agents or gel-forming agents, such as hydroxyalkyl cellulose or starch, and various carriers such as amorphous silica, alumina, or activated carbon.

In still another aspect, compositions comprising the substantially pure compound of formula 10 can be used in a spray-dried, co-dried, or microencapsulated form.

It should be appreciated that one of skill in the art would know how to incorporate the composition of the instant invention into a consumer good.

EXPERIMENTAL

The following examples are put forth so as to provide those of ordinary skill in the art with a complete disclosure and description of how the substantially pure ethyl ester of N-[[5-methyl-2-(1-methylethyl)cyclohexyl]carbonyl]glycine, and associated processes and methods are obtained, used, and/or evaluated, and are intended to be purely exemplary of the invention and are not intended to limit the scope of what the inventors regard as their invention. Efforts have been made to ensure accuracy with respect to numbers (e.g. amounts, temperature, etc.) and taste and cooling strength evaluations, but some errors and deviations should be accounted for. Unless indicated otherwise, parts are parts by weight, temperature is in ° C. (Celsius) or is at ambient temperature, and pressure is at or near atmospheric.

In accordance with the following examples, gas chromatographic analysis (GC) of products in all examples was conducted using a standard 30-m Stabilwax capillary column, a detector FID, and hydrogen carrier gas under the following conditions: starting temperature 100° C., program 15° C./min up to 240° C.

Further, the aqueous solutions of products for organoleptic tests were obtained by dissolving appropriate amounts of the products in dipropylene glycol DPG and adding the solution in DPG to an appropriate amount of water.

Comparative Synthetic and Organoleptic Example 1

Preparation and Purification of ethyl ester of N-[[5-methyl-2-(1-methylethyl) cyclohexyl]carbonyl]glycine 10 According to Example 2 of German Patent DE 2,205,255.

To a solution of sodium carbonate (21 g, 0.25 mole) and hydrochloride of glycine ethyl ester 12 (17.5 g, 0.125 mole) in 250 ml of water, was added a solution of p-menthoyl chloride 11 (25 g, 0.125 mole) in 125 ml of ether, and the resulting mixture was vigorously stirred for 2 hours. Then the ether layer was separated and dried with magnesium sulfate. The solvent was removed to give 31.7 g of an oily solid material, which was distilled under reduced pressure, and 25.4 g of ethyl ester of N-[[5-methyl-2-(1-methylethyl)cyclohexyl]carbonyl]glycine with a boiling range of 150° C. to 162° C. at ~0.1 torr. was collected as a yellow liquid which solidified in about one hour. The material was grinded to give a yellow powder with a melting point of 55–58° C. Analysis of this material using GC method showed a purity of only 86.93%, including 86.34% of the main isomer 10a and 0.59% of the neo isomer 10b. Detected impurities comprised: neomenthane-3-carboxylic acid 0.76%, p-menthane-3-carboxylic acid 5.91%, 3.89% of an unknown compound with retention time r.t. 13.9 minutes, 1.14% of unknown compound r.t. 23.1 minutes, balance 1.36% is distributed through 11 unknown compounds.

A visual and organoleptic test for a 25 ppm aqueous solution of the product obtained in this Example provided the following results: very pale yellow color, noticeable tingling/cooling sensation, and very noticeable bitter and sour taste and aftertaste.

Comparative Synthetic and Organoleptic Example 2

Preparation and Purification of ethyl ester of N-[[5-methyl-2-(1-methylethyl)cyclohexyl]carbonyl]glycine 10 According to Example 2 of British Patent GB 1,351,761 (Same or Similar Procedure is Given in U.S. Pat. Nos. 4,150,052; 4,178,459; 4,193,936; and 4,226,988).

Sodium bicarbonate (21 g, 0.25 mole) and glycine ethyl ester hydrochloride 12 (17.5 g, 0.125 mole) were dissolved in water (250 ml) and a solution of p-menth-3-oyl chloride 11 (25 g, 0.125 mole) in ether (125 ml) was added and the mixture was stirred vigorously at room temperature for 2 hours. At the end of this time the ether layer was separated and dried (MgSO$_4$). Removal of the solvent left an oily solid (30.8 g). This was distilled under reduced pressure, and 17.4 g of ethyl ester of N-[[5-methyl-2-(1-methylethyl)cyclohexyl]carbonyl]glycine with a boiling range of 150° C. to 152° C. at ~0.1 torr. was collected as a pale yellow liquid which solidified in about half an hour. The material was grinded to give a pale yellow powder with a melting point of 75–76° C. Analysis of this material using GC method showed a purity of 93.27%, including 92.63% of main isomer 10a and 0.64% of neo isomer 10b. The detected impurities comprised: neomenthane-3-carboxylic acid 0.09%, p-menthane-3-carboxylic acid 0.83%, 3.79% of an unknown compound with r.t. 13.9 min, 1.03% of unknown compound r.t. 23.1 minutes, balance 0.99% is distributed through 9 unknown compounds.

A visual and organoleptic test for a 25 ppm aqueous solution of the product obtained in this Example provided the following results: very pale yellow color, strong tingling/cooling sensation, and noticeable bitter and sour taste and aftertaste.

An additional redistillation of the product under the same conditions provided 12.7 g of very pale-yellowish material of 94.95% purity (including 94.30% of the main isomer 10a and 0.65% of the neo isomer 10b). The concentration of the unknown impurity r.t. 13.9 min remained practically unchanged (3.81%), which indicates the fact that this impurity is not possible to separate from the desired product by distillation.

The organoleptic properties of the product were also practically unchanged. A second visual and organoleptic test for a 25 ppm aqueous solution of the product obtained after the additional redistillation provided the following results: very pale yellow color, strong tingling/cooling sensation, and noticeable bitter and sour taste and aftertaste.

Inventive Example 1

Preparation, Additional Purification by Crystallization, and Organoleptic Valuation of ethyl ester of N-[[5-methyl-2-(1-methylethyl)cyclohexyl]carbonyl]glycine 10 According to the Invention.

Synthetic part. The synthetic part of this Example was conducted by following the procedure given in Example 2 of British Patent GB 1,351,761, in order to illustrate that the positive effect obtained in the present invention is not due to differences in the synthesis process between the instant disclosure and the methods disclosed in the prior art. Specifically, sodium bicarbonate (84 g, 1 mole) and glycine ethyl ester hydrochloride 12 (70 g, 0.5 mole) were dissolved in water (1 L) and a solution of p-menth-3-oyl chloride 11 (100 g, 0.5 mole) in ether (500 ml) was added and the mixture was stirred vigorously at room temperature for 2 hours. At the end of this time the ether layer was separated and dried (MgSO$_4$). Removal of the solvent left an oily solid (123.3 g). This was distilled under reduced pressure, and 72.0 g of ethyl ester of N-[[5-methyl-2-(1-methylethyl)cyclohexyl]carbonyl]glycine with a boiling range of 150° C. to 152° C. at ~0.1 torr. was collected as a pale yellow liquid which solidified in about half an hour. Analysis of this material using GC method showed a composition and purity very similar to the composition and purity given for the distilled product in the Comparative synthetic and organoleptic Example 2.

Additional purification step. Equipment used: glass crystallizer equipped with a stirrer, thermocouple for temperature control, reflux condenser, and cooling/heating glass jacket connected with a chiller/heater system with ethylene glycol/water mixture as a heat exchange medium.

The material obtained in the Synthetic part was melted, charged into the crystallizer, and dissolved in 145 g of heptane at 45–50° C. The obtained clear pale-yellow solution was stirred and slowly cooled down to about 0° C. which resulted in a massive crystallization of the product. The mixture was transferred quickly into a fritted (porous) glass filter, the crystals quickly filtered from the mother liquor, and air-dried on the filter to give 64.5 g of perfectly white crystals of ethyl ester of N-[[5-methyl-2-(1-methylethyl) cyclohexyl]carbonyl]glycine 10 with a melting range of 80.4–80.6° C. GC analysis showed a purity of 99.60%, including 98.38% of the main isomer 10a and 1.22% of the neo isomer 10b.

Visual and organoleptic test for a 25 ppm aqueous solution of the product obtained in this Example provided the following results: clear colorless solution, very strong tingling/cooling sensation, no bitter and sour taste or aftertaste.

Inventive Example 2

Preparation, Purification by Crystallization, and Organoleptic Evaluation of ethyl ester of N-[[5-methyl-2-(1-methylethyl)cyclohexyl]carbonyl]glycine 10.

In this example, the synthetic part and additional purification were conducted as in the Inventive Example 1, with the only difference that ethyl acetate was used instead of heptane as a solvent for crystallization. 28.7 g of ethyl ester of N-[[5-methyl-2-(1-methylethyl)cyclohexyl]carbonyl]glycine 10 was obtained as perfectly white crystals with a melting point of 80.9–81.0° C. GC analysis showed a purity of 99.68%, including 98.83% of the main isomer 10a and 0.85% of the neo isomer 10b.

Visual and organoleptic test for a 25 ppm aqueous solution of the product obtained in this Example provided the following results: clear colorless solution, very strong tingling/cooling sensation, no bitter and sour taste or aftertaste.

Inventive Example 3

Preparation, Purification by Double Crystallization, and Organoleptic Evaluation of ethyl ester of N-[[5-methyl-2-(1-methylethyl)cyclohexyl]carbonyl]glycine 10.

This example used a modified synthetic procedure followed by additional purification by double crystallization from heptane.

Synthesis step. To a solution of 70 g (0.66 mole) of sodium carbonate and 100 g (0.71 mole) of glycine ethyl ester hydrochloride 12 in 500 ml of water, was added dropwise a solution of p-menth-3-oyl chloride 11 (101 g, 0.5 mole) in 70 g of heptane. The mixture was stirred for 2 hours at room temperature and, after addition of 140 g of ethyl acetate, the layers were separated. The organic layer was washed with 250 g of 5% hydrochloric acid, then with 250 g of saturated aqueous Na bicarbonate solution and with water, then dried with Na sulfate. After rotary evaporation of the solvents, the residue was distilled under reduced pressure (b.p. 158–160° C. at about 0.5 torr) to give 107.8 g of crude distilled ethyl ester of N-[[5-methyl-2-(1-methylethyl) cyclohexyl]carbonyl]glycine 10.

Additional purification step part A. Crude ethyl ester of N-[[5-methyl-2-(1-methylethyl)cyclohexyl]carbonyl]glycine 10 was crystallized from 1100 g of heptane in a similar way as described in the Inventive Example 1 to give 91.7 g of ethyl ester of N-[[5-methyl-2-(1-methylethyl)cyclohexyl] carbonyl]glycine 10 containing by GC only main isomer 10a (99.24%), but also containing 0.76% of the unknown impurity r.t. 13.9 min.

Visual and organoleptic test (A) for a 25 ppm aqueous solution of this product provided the following results: clear colorless solution, very strong tingling/cooling sensation and weak bitter aftertaste.

Additional purification step part B. The product was additionally recrystallized from 300 g of hot heptane in a similar way as described above to give 87.0 g of ethyl ester of N-[[5-methyl-2-(1-methylethyl)cyclohexyl]carbonyl]glycine 10 containing only main isomer 10a (practically 100% by GC). Melting point of this material was 80.9–81.1° C.

Visual and organoleptic test (B) for a 25 ppm aqueous solution of the double-crystallized product provided the following results: clear colorless solution, extremely strong and pleasant tingling/cooling sensation, no bitter or sour taste or aftertaste.

Inventive Example 4

Preparation, Additional Purification by Precipitation, and Organoleptic Evaluation of ethyl ester of N-[[5-methyl-2-(1-methylethyl)cyclohexyl]carbonyl]glycine 10.

The Synthetic part of this example was performed as in the Inventive Example 3, but the additional purification part was performed differently (by precipitation). The crude distilled material was dissolved in a sufficient amount of ethanol, then precipitated with an excess amount of deionized water and filtered. The product obtained was air-dried on filter and then dried in vacuum to give 106.9 g of slightly off-white fine-granular solid with a melting range 78–80° C. Purity by GC: 96.12% of the main isomer 10a, 0.91% of the neo isomer 10b, and 0.98% of the unknown impurity r.t. 13.9 min, and the balance being other minor impurities.

Visual and organoleptic test for a 25 ppm aqueous solution of this product provided the following results: clear almost colorless solution, very strong tingling/cooling sensation. Also, exhibited was a somewhat bitter taste and aftertaste, but weaker than in the unpurified products of the prior art.

Inventive Example 5

Preparation, Additional Purification by Sublimation, and Organoleptic Evaluation of ethyl ester of N-[[5-methyl-2-(1-methylethyl)cyclohexyl]carbonyl]glycine 10.

The Synthetic part of this example was performed exactly as in the Inventive Example 3, but the Additional purification part was performed by a vacuum-sublimation. The sublimed material (white crystals) had a melting range of 79–80° C. and contained, according to GC, 98.37% of the main isomer 10a, 1.09% of the neo isomer 10b, and 0.25% of the unknown impurity r.t. 13.9 min, and the balance being other minor impurities.

Visual and organoleptic test for a 25 ppm aqueous solution of this product provided the following results: clear colorless solution, very strong tingling/cooling sensation and very weak bitter aftertaste, much weaker than in the unpurified products of the prior art.

Inventive Example 6

Comparison of the Cooling Strength of Highly Purified ethyl ester of N-[[5-methyl-2-(1-methylethyl)cyclohexyl]carbonyl]glycine 10 to the Cooling Strength of WS-3.

This example used the highly purified ethyl ester of N-[[5-methyl-2-(1-methylethyl)cyclohexyl]carbonyl]glycine 10 obtained in the Inventive Example 1.

A comparison basis aqueous solution of WS-3 (compound 5) was prepared containing 10 ppm concentration of WS-3.

Aqueous solutions were prepared containing various concentrations of the purified compound 10: 2 ppm, 3 ppm, 4 ppm, 5 ppm, and higher. These solutions were tested in oral application in comparison to the basis solution of 10 ppm of WS-3. It was found that the solution of 5 ppm of highly purified ethyl ester of N-[[5-methyl-2-(1-methylethyl)cyclohexyl]carbonyl]glycine 10 provided stronger and longer lasting cooling effect than the basis solution of 10 ppm of WS-3. It was also found that solution of 4 ppm of the highly purified ethyl ester of N-[[5-methyl-2-(1-methylethyl)cyclohexyl]carbonyl]glycine 10 provides approximately equal cooling effect to the basis solution of 10 ppm of WS-3.

Therefore, the highly purified ethyl ester of N-[[5-methyl-2-(1-methylethyl) cyclohexyl]carbonyl]glycine 10 of the Inventive Example 1 is approximately 2.5 times stronger than compound WS-3 (compound 5).

Inventive Example 7

Comparison of the Cooling Strength of Highly Purified ethyl ester of N-[[5-methyl-2-(1-methylethyl)cyclohexyl]carbonyl]glycine 10 to the Cooling Strength of WS-3.

This Example used the highly purified (double crystallized) ethyl ester of N-[[5-methyl-2-(1-methylethyl)cyclohexyl]carbonyl]glycine 10 obtained in the Inventive Example 3.

A comparison basis aqueous solution of WS-3 (compound 5) was prepared containing 10 ppm concentration of WS-3.

Aqueous solutions were prepared containing various concentrations of the purified compound 10: 2 ppm, 3 ppm, 3.5 ppm, 4 ppm, 5 ppm, and higher. These solutions were tested in oral application in comparison to the basis solution of 10 ppm of WS-3. It was found that the solution of 4 ppm of highly purified ethyl ester of N-[[5-methyl-2-(1-methylethyl)cyclohexyl]carbonyl]glycine 10 provided stronger and longer lasting cooling effect than the basis solution of 10 ppm of WS-3. It was also found that the solution of 3.5 ppm of the highly purified isomer 10a of ethyl ester of N-[[5-methyl-2-(1-methylethyl) cyclohexyl]carbonyl]glycine provides approximately equal cooling effect to the basis solution of 10 ppm of WS-3.

Therefore, the highly purified ethyl ester of N-[[5-methyl-2-(1-methylethyl) cyclohexyl]carbonyl]glycine 10 of the Inventive example 3 is approximately 3 times stronger than compound WS-3 (compound 5).

Throughout this application, various publications are referenced. The disclosures of these publications in their entireties are hereby incorporated by reference into this application.

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

The invention claimed is:

1. A composition comprising the ethyl ester of N-[[5-methyl-2-(1-methylethyl) cyclohexyl]carbonyl]glycine having the structure:

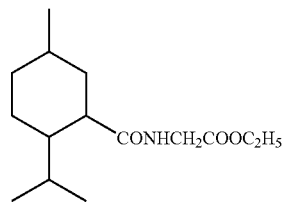

wherein the ethyl ester is at least 96% pure.

2. The composition of claim 1, comprising a plurality of stereoisomers.

3. The composition of claim 1, wherein the ethyl ester is at least 98% pure.

4. The composition of claim 1, wherein the ethyl ester is at least 99% pure.

5. The composition of claim 1, wherein the ethyl ester comprises at least 98% of the stereoisomer of the following configuration:

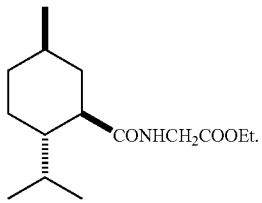

6. The composition of claim 1, wherein the ethyl ester comprises at least 99.5% of the stereoisomer of the following configuration:

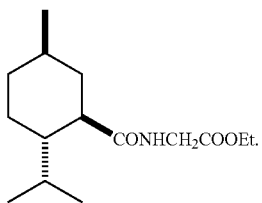

7. The composition of claim 1, wherein impurities causing a bitter and/or sour aftertaste are substantially absent.

8. A method for manufacturing the ethyl ester of claim 1, said method comprising purifying an impure ethyl ester of N-[[5-methyl-2-(1-methylethyl) cyclohexyl]carbonyl]glycine by at least one method selected from the group consisting of crystallization, sublimation, precipitation, and combinations thereof.

9. The method of claim 8, wherein the purified ethyl ester is at least 98% pure.

10. The mehtod of claim 8, wherein the purified ethyl ester is at least 99% pure.

11. A consumer product comprising the composition of claim 1.

12. The consumer product of claim 11, which is a flavor blend, food, confectionary, beverage, chewing gum, dental floss, toothpaste, mouthwash, anti-plaque composition, anti-gingivitis composition, throat lozenge, throat drop, antacid tablet, or a pharmaceutical or medical composition.

13. The consumer product of claim 11, which is a cosmetic, shampoo, lotion, deodorant, aftershave, shaving gel, shaving cream, fragrance, or soap.

* * * * *